US011071695B2

(12) United States Patent
Tadini D'Annolfo et al.

(10) Patent No.: US 11,071,695 B2
(45) Date of Patent: Jul. 27, 2021

(54) COSMETIC ANTI-BLEMISH COMPOSITION, USE OF THE COMPOSITION AND ANTI-BLEMISH TREATMENT METHOD

(71) Applicant: Natura Cosméticos S.A., São Paulo (BR)

(72) Inventors: Kassandra Tadini D'Annolfo, São Paulo (BR); Priscila Carollo Moncayo, São Paulo (BR); Eduardo Alexandre De Oliveira Reis, São Paulo (BR); Fabiana Paes, São Paulo (BR); Ricardo Augusto Santos De Oliveira, São Paulo (BR); Daniela Zimbardi, São Paulo (BR)

(73) Assignee: Natura Cosméticos S.A., São Paulo (BR)

( * ) Notice: Subject to any disclaimer, the term of this patent is extended or adjusted under 35 U.S.C. 154(b) by 0 days.

(21) Appl. No.: 16/312,105

(22) PCT Filed: May 24, 2017

(86) PCT No.: PCT/BR2017/050125
§ 371 (c)(1),
(2) Date: Dec. 20, 2018

(87) PCT Pub. No.: WO2018/032072
PCT Pub. Date: Feb. 22, 2018

(65) Prior Publication Data
US 2019/0240122 A1    Aug. 8, 2019

(30) Foreign Application Priority Data
Aug. 17, 2016  (BR) .......................... 102016019121-1

(51) Int. Cl.
| | | |
|---|---|---|
| *A61Q 19/08* | (2006.01) | |
| *A61Q 19/00* | (2006.01) | |
| *A61K 8/06* | (2006.01) | |
| *A61K 31/728* | (2006.01) | |
| *A61K 9/107* | (2006.01) | |
| *A61K 45/06* | (2006.01) | |
| *A61K 8/04* | (2006.01) | |
| *A61K 8/9789* | (2017.01) | |
| *A61K 8/34* | (2006.01) | |
| *A61K 8/58* | (2006.01) | |
| *A61K 8/892* | (2006.01) | |
| *A61K 8/894* | (2006.01) | |
| *A61K 8/895* | (2006.01) | |

(52) U.S. Cl.
CPC ................ *A61K 8/06* (2013.01); *A61K 8/345* (2013.01); *A61K 8/585* (2013.01); *A61K 8/892* (2013.01); *A61K 8/894* (2013.01); *A61K 8/895* (2013.01); *A61K 8/9789* (2017.08); *A61Q 19/001* (2013.01); *A61Q 19/08* (2013.01)

(58) Field of Classification Search
CPC .. A61K 2300/00; A61K 9/0014; A61K 9/107; A61K 8/06; A61K 9/10; A61K 2800/10; A61K 9/0019; A61K 8/25; A61K 31/728; A61K 8/062; A61Q 19/08; A61Q 19/00; A61Q 1/00; A61Q 19/001; A61Q 19/004; A61P 17/00
See application file for complete search history.

(56) References Cited

U.S. PATENT DOCUMENTS

| | | | | |
|---|---|---|---|---|
| 5,948,394 | A * | 9/1999 | Walling | A61K 8/585 424/63 |
| 6,685,952 | B1 * | 2/2004 | Ma | A61K 8/06 424/401 |
| 7,713,536 | B2 * | 5/2010 | Emig | A61K 8/064 424/401 |
| 2007/0048397 | A1 * | 3/2007 | Holland | A61K 31/198 424/764 |
| 2007/0071704 | A1 * | 3/2007 | Brillouet | A61K 8/06 424/70.12 |
| 2012/0282244 | A1 * | 11/2012 | Maestro | A61K 36/9068 424/115 |
| 2013/0336909 | A1 * | 12/2013 | Garaud | A61K 8/895 424/59 |
| 2014/0135406 | A1 * | 5/2014 | Lee | A61K 8/89 514/772.3 |
| 2015/0290109 | A1 * | 10/2015 | Simonnet | A61K 8/8117 132/206 |

FOREIGN PATENT DOCUMENTS

| | | |
|---|---|---|
| EP | 0326491 A1 | 8/1989 |
| JP | 2001/322940 A | 11/2001 |
| JP | 2003/055190 A | 2/2003 |
| WO | WO 2015/031971 A2 | 3/2015 |

OTHER PUBLICATIONS

International Search Report and Written Opinion for International Application No. PCT/BR2017/050125 dated Aug. 16, 2017.

* cited by examiner

*Primary Examiner* — Tracy Liu
(74) *Attorney, Agent, or Firm* — Alston & Bird LLP

(57) ABSTRACT

The present invention relates to cosmetic anti-blemish compositions, in the form of a silicone-containing emulsion, which are particularly useful to fill deep wrinkles, particularly around the lips.

9 Claims, 1 Drawing Sheet

COSMETIC ANTI-BLEMISH COMPOSITION, USE OF THE COMPOSITION AND ANTI-BLEMISH TREATMENT METHOD

FIELD OF THE INVENTION

The present invention relates to anti-aging cosmetic compositions in the form of a silicone emulsion, which are particularly useful to fill deep wrinkles, particularly on the lips.

PRIOR ART

The area of lips is considered a transition region between the oral mucosa and the skin around the lips. The lip skin has distinguishing physiological characteristics from the skin of other regions, such as for example, faster cell renewal and a very thin stratum corneum (the most superficial layer of the skin) (HIKIMA et al., 2004).

Some authors usually denominate the region between the skin and the mucosa of red region. This name is due to the color that is caused by the presence of numerous blood vessels. Since the epidermis in this region is very thin, this reflects on the reddish coloration. In addition, this area does not contain sweat glands responsible for the production of sweat—nor hair, but contains sebaceous glands—responsible for the production of sebum (ROOK, 2004).

Therefore, the area of the lips can be divided into three parts:
  External region: comprising the keratinized epidermis;
  Red region: comprising the thin epidermis;
  Mucosa: comprising the non-keratinized epidermis.

Since the epidermis of this region is less thick, it exposes the skin of the lips more intensely to environmental aggressions (sun, wind and cold), being more susceptible to dryness, and thus it may present cracks and intense flakiness.

Over the years the lip region undergoes changes that become visible, evidencing the aggressions suffered (BOSSET et al., 2002).

With aging the lips become thinner, without volume due to the decrease in thickness of the epidermis and dermis. To this effect is added the bone retraction of the region, which makes the lips even more retracted.

As with the skin on the rest of the face, the skin around the lips also loses elasticity, firmness and density due to changes in elastin, collagen and colloidal gel, which promote the appearance of fine wrinkles on the skin around the lips.

The fact that the skin of the lips and contour has smaller thickness in addition to the natural loss of skin thickness that occurs with aging and the constant movement of the site contributes to a greater appearance of wrinkles and expression lines. The first wrinkles in the lips region may appear around the age of 30 (KLIGMAN et al., 1985; LEVEQUE et al., 2004).

The lip region has deeper wrinkles (depth of from 250 to 400 micrometers), especially in the region of the nasogenian fold, known as "Chinese mustache" (BOSSET et al., 2002).

Cosmetic compositions that are known to be effective in reducing the amount of wrinkles in this region are still desired.

DESCRIPTION OF THE INVENTION

The present invention relates to anti-aging cosmetic compositions in the form of a silicone emulsion, which are particularly useful to fill deep wrinkles on the lips. This effect is obtained by combining hyaluronic acid-stimulating active ingredients, which is the major component responsible for assisting in filling the skin. The cosmetic compositions according to the present invention encourage the skin cells to produce hyaluronic acid and to fill wrinkles naturally, in addition to providing increased hydration by means of the uptake of water molecules to obtain maximum performance of the cosmetic treatment.

Figure 1A:
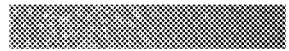
FIG. 1 shows skin with contrast on the cutaneous relief (FIG. 1A) versus skin with soft focus effect (FIG. 1B).
Figure 1B:
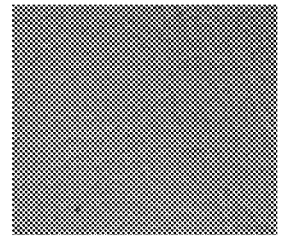

The cosmetic composition according to the present invention further provides the optical disguise or soft focus effect (as shown in FIG. 1).

Optical disguise is one of the key factors to obtain the makeup effect to disguise imperfections such as lines and wrinkles. These skin imperfections are only seen on the skin when there is contrast in the cutaneous relief. Microbeads, microscopical spherical or cylindrical particles, are known to reduce the contrast and to disguise skin imperfections conferring a natural look by means of the ability to spread the light while letting part of it pass. This phenomenon is known as soft focus or optical blurring, as shown in FIG. 1.

In addition, the compositions according to the present invention have a differentiated silicone emulsion texture which is characterized by ease of application, a velvety finish and by containing higher concentrations of active ingredients than ordinary cosmetic treatments.

The product forms a smooth film on the surface of the skin. The active ingredients permeate and interact with the skin to stimulate and protect its key mechanisms, cells and fibers to ensure skin filling, wrinkle reduction, firmness and elasticity.

The cosmetic compositions according to the present invention act on 11 major mechanisms responsible for the appearance of wrinkles. Namely:
1. Reposition of hyaluronic acid;
2. Optical disguise of wrinkles and imperfections;
3. Inhibition of microdamage;
4. Natural hydration restoration;
5. Hyaluronic acid stimulation;
6. Collagen stimulation;
7. Elastin stimulation;
8. Hyaluronic acid protection;
9. Elastin protection;
10. Protection of elastic fibers; and
11. Lipid protection.

This simultaneous action on 11 mechanisms is possible due to its active ingredients, which act in combination synergistically and simultaneously.

Thus, the anti-aging cosmetic compositions according to the present invention are provided in the form of a silicone emulsion comprising:
  a) at least one emollient;
  b) at least one humectant;
  c) at least one active ingredient;
  d) at least one emulsifier;
  e) at least one silicone; and
  f) cosmetically acceptable carriers.

The emollient is selected from the group consisting of hydrogenated polyisobutene, phenyl trimethicone, propylheptyl caprylate, caprylyl methicone, C12-15 alkyl benzoate, dibutyl adipate, dicaprylyl carbonate, isononyl isononanoate, dicapryl ether, dodecane, ethylhexyl palmitate, ethyl macadamate, isohexadecane, capric/caprylic triglyceride, butters from the Brazilian biodiversity, isoamyl cocoate or mixtures thereof. In a particular embodiment, the emollient is selected from the group consisting of hydrogenated polyisobutene, phenyl trimethicone, propylheptyl caprylate, or mixtures thereof.

The humectant is selected from the group consisting of glycerol, glycols, sorbitol, mannitol or mixtures thereof. In a particular embodiment, the humectant is glycerol.

The active ingredient is selected from the group comprising *Schinus terebinthifolius*, mixture of silanetriol/hyaluronic acid, mixture of sodium cocoyl amino acids/sarcosine/potassium aspartate/magnesium aspartate/propylene glycol, *Casearia sylvestris* extract, acetyl tetrapeptide-2, *Hymenaea courbaril* extract, a mixture of the *Paeonia albiflora* root extract, phenoxyethanol and ethylhexylglycerin, *Cichorium intybus* root extract, or mixtures thereof. In a particular embodiment the active ingredient is *Schinus terebinthifolius* extract, a mixture of silanetriol/hyaluronic acid, a mixture of sodium cocoyl amino acids/sarcosine/potassium aspartate/magnesium aspartate/propylene glycol, *Casearia sylvestris* extract, or mixtures thereof.

The emulsifier is selected from the group consisting of a mixture of cetyl PEG/PPG-10/dimethicone 90, polyglyceryl-4 isostearate, glyceryl citrate, potassium cetylphosphate, PEG-100, acrylates, xanthan gum, cetearyl alcohol, mixture of glyceryl stearate/PEG-100 or mixtures thereof. In a particular embodiment, it is a mixture of cetyl PEG/PPG-10/dimethicone 90, polyglyceryl-4 isostearate.

The silicone is selected from the group consisting of cyclopentasiloxane, a mixture of cyclopentasiloxane/dimethiconol, a mixture of cyclopentasiloxane/propylene carbonate, dimethicone/vinyl dimethicone crospolymer, dimethicone, or mixtures thereof. In a particular embodiment it is cyclopentasiloxane, a mixture of cyclopentasiloxane/dimethiconol, a mixture of cyclopentasiloxane/propylene carbonate, dimethicone/vinyl dimethicone crosspolymer, or mixtures thereof.

Cosmetically acceptable carriers may be selected from compounds known in the art.

Examples of carriers are: solvents, preservatives, perfumes/fragrances, polymer neutralizers, chelating agents, pH adjusters, among others.

In a particular embodiment, the compositions according to the present invention may further comprise a viscosity donor selected from magnesium sulphate, carbopol and/or the mixture of hydroethylacrylate/copolymer of sodium acryloyldimethyltaurate and squalene and polysorbate 60, particularly magnesium sulphate.

In another particular embodiment, the compositions according to the present invention may further comprise an absorbing agent selected from silica, a mixture of silica/titanium dioxide, or mixtures thereof.

The cosmetic compositions according to the present invention act on the signals, in addition to providing the optical disguise or soft focus effect.

Therefore, another object of the present invention consists of using the cosmetic compositions in an anti-aging treatment, particularly to fill wrinkles, more particularly, in the lip region.

Still another object of the present invention is an anti-aging treatment method as well as a method for filling wrinkles on the lips consisting of applying a cosmetically effective amount of the composition according to the present invention to the area of the lips at least once a day.

The following examples, without any limitation, illustrate the anti-aging cosmetic compositions according to the present invention, which surprisingly act simultaneously on the 11 major mechanisms responsible for the appearance of wrinkles, and provide an anti-aging effect and fill the wrinkles in the lip region.

EXAMPLES

Example 1. Composition According to the Present Invention

The following table illustrates the cosmetic compositions according to the present invention.

TABLE 1

| Anti-aging cosmetic compositions | | |
|---|---|---|
| Ingredient | Example A | Example B |
| aqua | 32.725 | 33.53 |
| Benzyl alcohol/Glycerin/Chlorphenesin | 1 | 0.80 |
| Cetyl PEG/PPG-10/1/Dimethicone 90 | 2.5 | 2.70 |
| Cyclopentasiloxane | 17 | 15.00 |
| Cyclopentasiloxane/Dimethiconol | 1 | 3.00 |
| Cyclopentasiloxane/propylene carbonate | 2.8 | 1.50 |
| Dimethicone/Vinyl Dimethicone Crosspolymer | 5 | 6.50 |
| Glycerin (glycerol) | 6 | 8.00 |
| Hydrogenated Polyisobutene | 4 | 2.00 |
| Magnesium Sulfate | 1 | 1.00 |
| Phenyl Trimethicone | 0.35 | 0.45 |
| Polyglyceryl-4 isostearate | 2.5 | 2.40 |
| Propylheptyl caprylate | 6 | 4.50 |
| *Schinus terebinthifolius* Extract | 0.025 | 0.02 |
| Silanetriol/Hyaluronic acid | 5 | 4.20 |
| Silica/Titanium dioxide | 7.5 | 9.00 |
| Silica Dimethyl Silylate | 0.5 | 0.20 |
| Silica Pearls | 2 | 1.00 |
| Sodium Cocoyl Amino Acids/Sarcosine/Potassium Aspartate/Magnesium Aspartate/Water/Propylene Glycol | 3 | 4.00 |
| Water/*Casearia sylvestris* Extract/Silica | 0.1 | 0.20 |
| Total | 100.00 | 100.00 |

Example 2. Evaluation of the Efficacy of a Cosmetic Product Through Instrumental Measurements Under Normal Use Conditions The survey participants (women aged from 38 to 70 years—average of 59 years—having wrinkled of grades II to IV) were evaluated by a dermatologist in the beginning of the study (D0) to verify the inclusion and exclusion criteria and were also evaluated in the end of the study to verify possible reactions or discomforts experienced while using the product.

After the initial medical evaluation images of the periorbital, nasogenian, and frontal regions were obtained using Optical 3D Skin Measuring Device PRIMOS Compact 5.075. The obtained images of the periorbital and nasogenian regions were performed randomly.

After acquisition of the initial images the product was applied under supervision to all participants.

New images using Optical 3D Skin Measuring Device PRIMOS Compact 5.075 were performed 15 minutes after application of the product (Immediate) and after 7, 14, 28 and 56 days (+/−2 days) of use of the product.

Participants were instructed to use the product at home according to the provided instructions for 56 days (+/−2 days).

The participants were allowed to rest in a temperature- and relative humidity-controlled room (20° C.±2° C. and 50%±5 RH) for 30 minutes prior to the measurements and while performing the measurements.

Periorbital Region:

The product caused a reduction in the parameters of volume of wrinkles, average roughness (Ra), average depth (Rz), maximum roughness (R m), rippling (Wt) and wrinkle depth just after application of the product and after seven, fourteen, twenty-eight and fifty-six days of use.

The product caused a reduction in the texture parameter immediately after application of the product and after 14 days of use.

Frontal Region:

The product caused a reduction in the parameters of average roughness (Ra), average depth (Rz), maximum roughness (Rm), rippling (Wt), wrinkle depth and texture immediately after application of the product.

The product caused a reduction in wrinkle volume after fifty-six days of use.

Nasolabial Region:

The product caused a reduction in the parameters of average roughness (Ra), average depth (Rz), maximum roughness (Rm), rippling (Wt), wrinkle depth and texture immediately after application of the product.

Example 3. Evaluation of the Efficacy of a Cosmetic Product Through the Efficacy Perceived by the Survey Participant and the Evaluation of Dermatological Clinical Efficacy Under Normal Use Conditions The survey participants were evaluated by a dermatologist in the beginning of the study (D0) to verify the inclusion and exclusion criteria and were also evaluated in the end of the study to verify possible reactions or discomforts experienced while using the product.

The included participants were clinically evaluated by the dermatologist for the initial state of the face skin and were later instructed to answer a self-assessment questionnaire on the initial state of the face skin (D0).

After inclusion and application of the initial questionnaire, the product was applied under supervision to all participants.

After the first application of the product, evaluations of perceived and clinical efficacy were performed through questionnaires 10 minutes after applying the product in the Institute (Immediate) and after 7, 14, 28 and 56 days (+/−2 days) of use of the product.

The participants (women aged 39 to 70 years—average of 55 years—having wrinkles of grades II to V) were instructed to use the product at home as per the provide instructions for 56 days (+/−2 days).

Assessment of Perceived Efficacy:

An improvement in "expression lines/signs (fine lines) in the region of the 'Chinese Mustache' and in the overall appearance" was observed at D14 as compared to D7;

An improvement in "expression lines/signs (fine lines) in the region of the forehead, in expression lines/signs (fine lines) in the region of the Chinese Mustache, and in the overall appearance was observed at D28 as compared to D7;

An improvement in "wrinkles (deep lines), in expression lines/signs (fine lines) in the region of the forehead, in expression lines/signs (fine lines) in the region of the Chinese Mustache, and in the overall appearance was observed at D56 as compared to D7;

An improvement in "expression lines/signs (fine lines) in the region of the forehead and in the overall appearance was observed at D56 as compared to D14;

An improvement in the "overall appearance" was observed at D56 compared to D28.

Immediate:

18% of the participants perceived "filling of wrinkles (deep lines) in the region of the eyes";

20% of the participants perceived "filling of wrinkles (fine lines) in the region of the eyes";

15% of the participants perceived "filling of wrinkles in the region of the lips";

16% of the participants perceived "filling of wrinkles in the region of the Chinese Mustache";

25% of the participants perceived "filling of wrinkles in the region of the forehead";

36% of participants reported improved overall appearance".

D7:

41% of the participants reported a reduction in "wrinkles (deep lines)" on the skin;

51% of the participants reported a reduction in expression lines/signs (fine lines) in the region of the eyes;

43% of the participants reported a reduction in expression lines/signs (fine lines) in the region of the forehead;

41% of the participants reported a reduction in "expression lines/signs (fine lines) in the region of the lips";

31% of the participants reported a reduction in "expression lines/signs (fine lines) in the region of the 'Chinese Mustache'";

72% of the participants reported an improvement in the overall appearance of the skin (bright, revitalized, rebalanced, healthy looking skin)";

D14:

49% of the participants reported a reduction in "wrinkles (deep lines)" on the skin;

52% of the participants reported a reduction in expression lines/signs (fine lines) in the region of the eyes;

48% of the participants reported a reduction in expression lines/signs (fine lines) in the region of the forehead;

51% of the participants reported a reduction in "expression lines/signs (fine lines) in the region of the lips";

46% of the participants reported a reduction in "expression lines/signs (fine lines) in the region of the 'Chinese Mustache'";

77% of the participants reported an improvement in the "overall appearance of the skin (bright, revitalized, rebalanced, healthy looking skin)".

D28:

52% of the participants reported a reduction in "wrinkles (deep lines)" on the skin;

56% of the participants reported a reduction in expression lines/signs (fine lines) in the region of the eyes;

54% of the participants reported a reduction in expression lines/signs (fine lines) in the region of the forehead;

49% of the participants reported a reduction in "expression lines/signs (fine lines) in the region of the lips";

49% of the participants reported a reduction in "expression lines/signs (fine lines) in the region of the 'Chinese Mustache'";

84 of the participants reported an improvement in the "overall appearance of the skin (bright, revitalized, rebalanced, healthy looking skin)";

D56:

59% of the participants reported a reduction in "wrinkles (deep lines)" on the skin;

63% of the participants reported a reduction in expression lines/signs (fine lines) in the region of the eyes;

61% of the participants reported a reduction in "expression lines/signs (fine lines) in the region of the forehead";

58% of the participants reported a reduction in "expression lines/signs (fine lines) in the region of the lips";

51% of the participants reported a reduction in "expression lines/signs (fine lines) in the region of the 'Chinese Mustache'";

88% of the participants reported an improvement in the "overall appearance of the skin (bright, revitalized, rebalanced, healthy looking skin)".

Assessment of Clinical Efficacy

Comparison with D0:

Worsening of the "healthy appearance" was observed at Immediate as compared with D0;

An improvement in the "signs of aging" was observed at Immediate as compared with D0.

An improvement in "expression lines/signs (fine lines)—nasogenian, signs of aging, overall appearance and healthy appearance" was observed at D7 as compared to D0;

An improvement in "expression lines/signs (fine lines)—Periorbital, expression lines/signs (fine lines) in the forehead region, expression lines/signs in the nasogenian region, expression lines/signs (fine lines)—around the lips, the signs of aging, the overall appearance and healthy appearance" was observed at D14 and D28 as compared to T0;

An improvement in the "degree of wrinkles (periorbital), in expression lines/signs in the Periorbital region, expression lines/signs in the forehead region, expression lines/signs in the nasogenian region, expression lines/signs in the region around the lips, signs of aging, overall appearance and healthy appearance" was observed at D56 as compared to D0.

Comparison with Immediate:

An improvement in overall appearance and healthy appearance was observed in D7 as compared to Immediate;

An improvement in "expression lines/signs in the periorbital region, expression lines/signs around the lips, signs of aging, overall appearance and healthy appearance" was observed at D14 as compared to Immediate;

An improvement in the "expression lines/signs in the periorbital region, in expression lines/signs in the forehead region, expression lines/signs in the nasogenian region, expression lines/signs in the region around the lips, signs of aging, overall appearance and healthy appearance" was observed at D28 as compared to Immediate;

An improvement in the "degree of wrinkles (periorbital), in expression lines/signs in the periorbital region, expression lines/signs in the forehead region, expression lines/signs in the nasogenian region, expression lines/signs in the region around the lips, signs of aging, overall appearance and healthy appearance" was observed at D56 as compared to Immediate.

Comparison with D7:

An improvement in the "expression lines/signs in the periorbital region, in expression lines/signs in the forehead region, expression lines/signs around the lips, signs of aging, overall appearance and healthy appearance" was observed at D14 as compared to D7;

An improvement in the "expression lines/signs in the periorbital region, in expression lines/signs in the forehead region, expression lines/signs in the nasogenian region, expression lines/signs in the region around the lips, signs of aging, overall appearance and healthy appearance" was observed at D28 as compared to D7;

An improvement in the "degree of wrinkles (periorbital), in expression lines/signs in the periorbital region, expression lines/signs in the forehead region, expression lines/signs in the nasogenian region, expression lines/signs in the region around the lips, signs of aging, overall appearance and healthy appearance" was observed at D56 as compared to D7.

Comparison with D14:

An improvement in "expression lines/signs in the periorbital region, expression lines/signs around the lips, signs of aging, overall appearance and healthy appearance" was observed at D28 as compared to D14;

An improvement in the "degree of wrinkles (periorbital), in expression lines/signs in the Periorbital region, expression lines/signs in the forehead region, expression lines/signs in the nasogenian region, expression lines/signs in the region around the lips, signs of aging, overall appearance and healthy appearance" was observed at D56 as compared to D14.

Comparison with D28:

An improvement in the "degree of wrinkles (periorbital), in expression lines/signs in the periorbital region, expression lines/signs in the forehead region, expression lines/signs around the lips, signs of aging, overall appearance and healthy appearance" was observed at D56 as compared to D28.

The person skilled in the art, by means of the teachings of the text and examples disclosed herein, will readily appreciate the advantages of the invention and will propose equivalent embodiment variations and alternatives without departing from the scope of the invention as defined in the appended claims.

The invention claimed is:

1. An anti-aging cosmetic composition comprising a silicone emulsion, the silicone emulsion comprising:
   a) at least one emollient selected from the group consisting of hydrogenated polyisobutene, phenyl trimethicone, propylheptyl caprylate, caprylyl methicone, C12-15 alkyl benzoate, dibutyl adipate, dicaprylyl carbonate, isononyl isononanoate, dicapryl ether, dodecane, ethylhexyl palmitate, ethyl macadamate, isohexadecane, capric/caprylic triglyceride, butters from Brazilian biodiversity, isoamyl cocoate, and mixtures thereof;
   b) at least one humectant selected from the group consisting of glycerol, glycols, sorbitol, mannitol, and mixtures thereof;
   c) active ingredients comprising 0.025% *Schinus terebinthifolius* extract; 5% of a mixture of silanetriol and hyaluronic acid; and 0.1% *Casearia sylvestris* extract;
   d) at least one emulsifier selected from the group consisting of a mixture of cetyl PEG, PPG-10, and dimethicone 90; polyglyceryl-4 isostearate; glyceryl citrate; potassium cetylphosphate; PEG-100; acrylates; xanthan gum; cetearyl alcohol; a mixture of glyceryl stearate and PEG-100; and mixtures thereof;
   e) at least one silicone selected from the group consisting of cyclopentasiloxane; a mixture of cyclopentasiloxane and dimethiconol; a mixture of cyclopentasiloxane and propylene carbonate; dimethicone/vinyl dimethicone crosspolymer; dimethicone; and mixtures thereof; and
   f) cosmetically acceptable carriers.

2. The composition of claim 1, wherein the humectant is glycerol.

3. The composition of claim 1, wherein the emulsifier is a mixture of cetyl PEG, PPG-10, and dimethicone 90; or polyglyceryl-4 isostearate.

4. The composition of claim 1, further comprising a viscosity donor selected from the group consisting of magnesium sulphate; carbopol; and a mixture of hydroethylacrylate/sodium acryloyldimethyltaurate copolymer, squalene, and polysorbate 60.

5. The composition of claim 4 wherein the viscosity donor is magnesium sulfate.

6. The composition of claim 1, further comprising an absorbing agent selected from the group consisting of silica and a mixture of silica and titanium dioxide.

7. An anti-aging treatment method, the method consisting of applying a cosmetically effective amount of the composition of claim 1 to a patient.

8. The anti-aging treatment method of claim 7, the method consisting of applying a cosmetically effective amount of the composition as defined in claim 1 to the area of the lips at least once a day.

9. The method of claim 8, wherein the anti-aging treatment method is for filling wrinkles in the region of the lips.

* * * * *